United States Patent
Wheatley et al.

(10) Patent No.: US 9,592,337 B2
(45) Date of Patent: *Mar. 14, 2017

(54) DEVICE FOR AT LEAST ONE OF INJECTION OR ASPIRATION

(75) Inventors: Barry Lynn Wheatley, Oceanside, CA (US); Brian William McDonell, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1659 days.

This patent is subject to a terminal disclaimer.

(21) Appl. No.: 13/096,838

(22) Filed: Apr. 28, 2011

(65) Prior Publication Data

US 2012/0165783 A1 Jun. 28, 2012

Related U.S. Application Data

(63) Continuation-in-part of application No. 12/976,038, filed on Dec. 22, 2010, now Pat. No. 8,535,268.

(51) Int. Cl.
*A61M 5/142* (2006.01)
*A61M 5/145* (2006.01)
(Continued)

(52) U.S. Cl.
CPC .......... *A61M 5/1452* (2013.01); *A61F 9/007* (2013.01); *A61M 5/20* (2013.01); *A61M 5/2053* (2013.01);
(Continued)

(58) Field of Classification Search
CPC .............. A61M 5/14216; A61M 2205/14533; A61M 5/31583
See application file for complete search history.

(56) References Cited

U.S. PATENT DOCUMENTS 3,101,711 A 8/1963 Reitknecht
3,517,668 A 6/1970 Brickson
(Continued)

FOREIGN PATENT DOCUMENTS

AU 2002242864 10/2002
AU 2002249383 10/2002
(Continued)

OTHER PUBLICATIONS

International Search Report for PCT/US2011/062780, dated Apr. 3, 2012, 2 pages.

(Continued)

*Primary Examiner* — Matthew F Desanto
(74) *Attorney, Agent, or Firm* — Darien Reddick

(57) ABSTRACT

Micro-volume devices, systems, and associated methods that facilitate the injection or aspiration of precisely controlled volumes of materials at precisely controlled rates are provided. In one embodiment, a micro-volume device includes a syringe and a lead screw connected to a plunger of the syringe. A mechanical interface is connected to the lead screw and includes a first set of cams adjacent a proximal portion and a second set of cams adjacent a distal portion. A mechanism is configured to oscillate a structure in a direction parallel to a longitudinal axis of the lead screw such that one or more projections of the structure to alternatively engage cams of the first and second sets of cams in a manner that results in rotation of the mechanical interface in a single direction for highly controlled linear displacement of the plunger.

27 Claims, 11 Drawing Sheets

(51) Int. Cl.
  *A61M 5/20* (2006.01)
  *A61F 9/007* (2006.01)
  *A61M 5/315* (2006.01)
(52) U.S. Cl.
  CPC .. *A61M 5/31583* (2013.01); *A61M 2205/0294* (2013.01); *A61M 2209/01* (2013.01); *A61M 2210/0612* (2013.01)

(56) References Cited

U.S. PATENT DOCUMENTS

| | | |
|---|---|---|
| 3,745,843 A | 7/1973 | Hetzel |
| 3,790,048 A | 2/1974 | Luciano et al. |
| 4,022,207 A | 5/1977 | Citrin |
| 4,230,025 A | 10/1980 | Caliri |
| 4,270,399 A | 6/1981 | Knief |
| 4,367,739 A | 1/1983 | LeVeen et al. |
| 4,498,904 A | 2/1985 | Turner et al. |
| 4,589,870 A | 5/1986 | Citrin et al. |
| 4,659,327 A | 4/1987 | Bennett et al. |
| 4,678,408 A | 7/1987 | Nason et al. |
| 4,681,102 A | 7/1987 | Bartell |
| 4,834,094 A | 5/1989 | Patton et al. |
| 4,865,591 A | 9/1989 | Sams |
| 4,936,833 A | 6/1990 | Sams |
| 5,017,190 A | 5/1991 | Simon et al. |
| 5,336,201 A | 8/1994 | von der Decken |
| 5,354,268 A | 10/1994 | Peterson et al. |
| 5,354,333 A | 10/1994 | Kammann et al. |
| 5,370,630 A | 12/1994 | Smidebush et al. |
| 5,425,734 A | 6/1995 | Blake |
| 5,468,246 A | 11/1995 | Blake |
| 5,507,727 A | 4/1996 | Crainich |
| 5,582,614 A | 12/1996 | Feingold |
| 5,607,433 A | 3/1997 | Polla et al. |
| 5,629,577 A | 5/1997 | Polla et al. |
| 5,643,275 A | 7/1997 | Blake |
| 5,643,276 A | 7/1997 | Zaleski |
| 5,743,889 A | 4/1998 | Sams |
| 5,807,346 A | 9/1998 | Frezza |
| 5,868,728 A | 2/1999 | Giungo et al. |
| 5,868,751 A | 2/1999 | Feingold |
| 5,891,153 A | 4/1999 | Peterson |
| 5,961,496 A | 10/1999 | Nielsen et al. |
| 6,004,297 A | 12/1999 | Steenfeldt-Jensen et al. |
| 6,102,895 A | 8/2000 | Cortella et al. |
| 6,162,230 A | 12/2000 | Polla et al. |
| 6,179,843 B1 | 1/2001 | Weiler |
| 6,235,004 B1 | 5/2001 | Steenfeldt-Jensen et al. |
| 6,277,096 B1 | 8/2001 | Cortella et al. |
| 6,280,449 B1 | 8/2001 | Blake |
| 6,497,708 B1 | 12/2002 | Cumming |
| 6,503,275 B1 | 1/2003 | Cumming |
| 6,558,395 B2 | 5/2003 | Hjertman et al. |
| 6,585,699 B2 | 7/2003 | Ljunggreen et al. |
| 6,592,591 B2 | 7/2003 | Polla et al. |
| 6,595,956 B1 | 7/2003 | Gross et al. |
| 6,656,158 B2 | 12/2003 | Mahoney et al. |
| 6,666,871 B2 | 12/2003 | Kikuchi et al. |
| 6,673,049 B2 | 1/2004 | Hommann et al. |
| 6,899,698 B2 | 5/2005 | Sams |
| 7,066,909 B1 | 6/2006 | Peter et al. |
| 7,195,613 B2 | 3/2007 | Woolston |
| 7,198,615 B2 | 4/2007 | Langley et al. |
| 7,384,413 B2 | 6/2008 | Gross et al. |
| 7,390,314 B2 | 6/2008 | Stutz, Jr. et al. |
| 7,513,889 B2 | 4/2009 | Jost |
| 7,615,056 B2 | 11/2009 | Ayton et al. |
| 7,794,430 B2 | 9/2010 | Langley et al. |
| 7,922,695 B2* | 4/2011 | Wiegel et al. ............... 604/155 |
| 8,535,268 B2* | 9/2013 | Auld et al. .................... 604/151 |
| 2001/0007075 A1 | 7/2001 | Hjertman et al. |
| 2002/0111587 A1 | 8/2002 | Hommann et al. |
| 2003/0040755 A1 | 2/2003 | Meyer |
| 2003/0139749 A1 | 7/2003 | Kikuchi et al. |
| 2003/0199824 A1* | 10/2003 | Mahoney et al. ............ 604/155 |
| 2003/0216745 A1 | 11/2003 | Brady et al. |
| 2003/0236498 A1 | 12/2003 | Gross et al. |
| 2004/0147938 A1 | 7/2004 | Dusek et al. |
| 2004/0160575 A1 | 8/2004 | Ayton et al. |
| 2004/0215207 A1 | 10/2004 | Cumming |
| 2005/0055011 A1 | 3/2005 | Enggaard |
| 2005/0085776 A1 | 4/2005 | Hommann et al. |
| 2006/0085013 A1 | 4/2006 | Dusek et al. |
| 2006/0229633 A1 | 10/2006 | Shepherd |
| 2006/0229634 A1 | 10/2006 | Shepherd |
| 2006/0247581 A1 | 11/2006 | Pedersen et al. |
| 2006/0263511 A1 | 11/2006 | Musch et al. |
| 2007/0043319 A1 | 2/2007 | Kimmel et al. |
| 2008/0214996 A1 | 9/2008 | Kimmell et al. |
| 2008/0215005 A1 | 9/2008 | Gross et al. |
| 2008/0312605 A1 | 12/2008 | Saiki |
| 2009/0018512 A1 | 1/2009 | Charles |
| 2009/0105650 A1 | 4/2009 | Wiegel et al. |
| 2009/0118738 A1 | 5/2009 | Gerondale |
| 2009/0254045 A1 | 10/2009 | Jost |
| 2010/0145275 A1 | 6/2010 | Grunhut et al. |

FOREIGN PATENT DOCUMENTS

| | | |
|---|---|---|
| CA | 2439900 | 10/2002 |
| CA | 2582976 | 4/2006 |
| DE | 280192 | 11/1914 |
| DE | 836703 | 4/1952 |
| DE | 29818721 | 4/2000 |
| EP | 0270257 | 6/1988 |
| EP | 0363213 | 4/1990 |
| EP | 0295075 | 12/1991 |
| EP | 0477466 | 6/1996 |
| EP | 0673482 | 4/1998 |
| EP | 1011561 | 6/2000 |
| EP | 1003581 | 11/2000 |
| EP | 1358856 | 11/2003 |
| EP | 0925082 | 1/2005 |
| EP | 1276529 | 6/2006 |
| EP | 1698365 | 9/2006 |
| EP | 1372770 | 11/2006 |
| EP | 1372767 | 1/2007 |
| EP | 1372771 | 1/2007 |
| EP | 1799287 | 6/2007 |
| EP | 1332731 | 8/2007 |
| GB | 2224214 | 5/1990 |
| JP | 2005523120 | 8/2005 |
| NZ | 554384 | 4/2010 |
| WO | WO 94/07562 | 4/1994 |
| WO | WO 94/15120 | 7/1994 |
| WO | 97/36623 | 10/1997 |
| WO | WO 98/57686 | 12/1998 |
| WO | WO 01/78812 | 10/2001 |
| WO | WO 02/076536 | 10/2002 |
| WO | WO 02/076537 | 10/2002 |
| WO | WO 02/076539 | 10/2002 |
| WO | WO 02/081009 | 10/2002 |
| WO | 03090819 | 11/2003 |
| WO | WO 2004/035113 | 4/2004 |
| WO | WO 2004/091447 | 10/2004 |
| WO | WO 2004/112871 | 12/2004 |
| WO | WO 2005/020853 | 3/2005 |
| WO | WO 2005/070483 | 8/2005 |
| WO | WO 2006/037434 | 4/2006 |
| WO | WO 2006/113138 | 10/2006 |
| WO | WO 2006/113357 | 10/2006 |
| WO | WO 2008/020023 | 2/2008 |
| WO | WO 2008/059385 | 5/2008 |
| WO | WO 2008/155144 | 12/2008 |
| WO | 2009125398 | 10/2009 |

(56) References Cited

FOREIGN PATENT DOCUMENTS

| WO | WO 2010/066796 | 6/2010 |
|---|---|---|
| WO | WO 2010/066797 | 6/2010 |

OTHER PUBLICATIONS

Written Opinion of the International Searching Authority, International Application No. PCT/US2011/062780, dated Apr. 3, 2012, 6 pages.
International Search Report and Written Opinion of the International Searching Authority, International Application No. PCT/2011/062776, dated Mar. 22, 2012, 8 pages.
International Preliminary Report on Patentability and Written Opinion of the International Searching Authority, International Application No. PCT/2011/062776, dated Mar. 22, 2012, 7 pages.
International Preliminary Report on Patentability and Written Opinion of the International Searching Authority, International Application No. PCT/2011/062780, dated Jun. 25, 2012, 7 pages.
Supplementary European Search Report for Application No. 11851735.8, Publication No. 2654859, Published Oct. 30, 2013, 6 pages.
Supplementary European Search Report for Application No. 11851259.9, Publication No. EP2654826, Published Oct. 30, 2013, 7 pages.

* cited by examiner

DEVICE FOR AT LEAST ONE OF INJECTION OR ASPIRATION

CROSS-REFERENCE TO RELATED APPLICATIONS

This application is a continuation-in-part of prior application Ser. No. 12/976,038, filed Dec. 22, 2010, which is incorporated herein by reference in its entirety.

TECHNICAL FIELD

The present disclosure relates generally to material delivery and/or aspiration and, more particularly, to material delivery and/or aspiration associated with ophthalmic surgery and ophthalmic drug delivery.

During ophthalmic surgery, a need exists to inject fluids into the eye at very precise volumes, at very precise flow rates, and at very specific locations within the eye. Presently, ophthalmic injections are typically manually made using a conventional syringe and needle. However, such injections can lead to tissue damage, caused by, for example, "unsteady" injections. Additionally, the volume of material injected in this manner is difficult to control because the scale on the syringe is generally not accurate relative to the small injection volume. Additionally, positioning and actuating the needle with a single hand also poses difficulty for a medical practitioner. Accuracy of the amount of material is also reduced because of parallax error. Further, the fluid flow rates of such syringes are also difficult to control since the flow rate of material from the syringe is controlled by the force asserted by the operator. Still further, controlling an amount of material injected into the eye may be limited by the ability of the operator accurately to stop the injection when the desired amount of material has been injected.

Accordingly, there exists a need for devices, systems, and associated methods, for use in injecting and/or aspirating materials during a medical procedure that facilitate the injection or aspiration of precisely controlled volumes of materials at precisely controlled rates.

SUMMARY

One aspect of the present disclosure encompasses an apparatus including a body defining a cavity for receiving a fluid, a structure moveable within the cavity, a lead screw, a cam device coupled to the lead screw and having a plurality of cams, at least one engaging member adapted to engage the plurality of cams, and an actuator coupled to the at least one engaging member. The body may include a first opening providing communication between the cavity and an exterior of the body. The structure may be adapted to be displaced within the cavity to displace an amount of material within the cavity. The lead screw may include a first portion coupled to the structure and a longitudinal axis. The actuator may be operable to oscillate the at least one engaging member to alternately engage the plurality of cams so as to rotate the cam device in a single direction.

Another aspect of the present disclosure encompasses a body including a first cavity for receiving a fluid. The body may also include a first opening providing communication between with the cavity and an exterior of the body, a second cavity, and a bore extending along a longitudinal axis. The bore may provide communication between the first cavity and the second cavity. The apparatus may also include a structure movable within the cavity. The structure may be adapted to be displaced within the cavity to displace an amount of the material within the cavity. The apparatus may also include a lead screw extending along the longitudinal axis through the bore, and a cam device disposed in the second cavity and rotatable therein. The lead screw may include a first portion coupled to the structure. The cam device may be coupled to the lead screw, and the cam device may include a plurality of cams. The apparatus may also include at least one engaging member adapted to engage the plurality of cams, and an actuator coupled to the at least on engaging member, the actuator operable to oscillate the at least one engaging member to alternately engage the plurality of cams so as to rotate the cam device in a single direction.

A further aspect of the disclosure encompasses a method for one of injecting or aspirating material. The method may include oscillating at least one engagement member relative to a cam device, the cam device including a first plurality of cams and a second plurality of cams angularly offset from each other about a longitudinal axis; engaging the at least one engaging member with the first plurality of cams in a first direction of the oscillation to rotate the cam device in a first direction; engaging the at least one engaging member with the second plurality of cams in a second direction of the oscillation, the second direction opposite the first direction, to rotate the cam device in the first direction; coupling a lead screw with the cam device such that the lead screw is longitudinally moveable relative to the cam device and rotationally fixed relative to the cam device; and displacing the lead screw longitudinally relative to the cam device as the cam device is rotated in the first direction.

The various aspects may include one or more of the following features. The plurality of cams may include a first plurality of cams disposed proximate a first end of the cam device and a second plurality of cams disposed proximate a second end of the cam device. The at least one engaging member may engage one of the first plurality of cams when the at least one engaging member is moved towards the first end of the cam device to cause the cam device to rotate in a first angular direction, and the at least one engaging member may engage one of the plurality of the second plurality of cams when the at least one engaging member is moved towards the second end of the cam device to cause the cam device to rotate in the first angular direction. Each cam of the plurality of cams may include an engagement surface operable contact the at least one engaging member. The engaging surface may include a slope to cause a rotation to the cam device as the at least one engaging member slides along the engagement surface. The first plurality of cams and the second plurality of cams may be rotationally offset from each other about the longitudinal axis. The apparatus may also include an advancement component. The advancement component may include a first engaging feature. The lead screw may include a second engaging feature, and the first engaging feature and the second engaging feature may be adapted to matingly engage to cause the lead screw to translate longitudinally along the longitudinal axis when the lead screw is rotated. The first engaging feature may be a threaded portion, and the second engaging feature may be an outer threaded surface. The advancement component may include a slot, and the first engaging feature may be formed on an interior surface of the slot.

The housing may include a slot. The advancement component may be slideable within the slot between a first position in which the first engaging feature is engaged with the second engaging feature and a second position in which the first engaging feature is not engaged with the second engaging feature. The cam device may also include a central passage defining an interior wall, and a protrusion extending inwardly from the interior wall. The cam device may include a longitudinally extending slot, and the cam device may be coupled to the lead screw by receipt of the protrusion into the longitudinally extending slot. The lead screw is longitudinally slideable within a passage formed within the cam device. The lead screw may be rotationally fixed within the cam device. The apparatus may also include an outer collar disposed circumjacent to the cam device. The at least one engaging member may extend radially from an interior surface of the outer collar. The outer collar may be coupled to the actuator and operable to move longitudinally relative to the cam device. The apparatus may also include a needle that defines a lumen. The needle may be coupled to the body such that the lumen is in communication with the first opening.

Various aspects may also include one or more of the following features. The apparatus may include an outer collar disposed within the second cavity and coupled to the actuator. The outer collar may include a central bore defining an interior surface. The cam device may be disposed in the central bore, and the at least one engaging member may extend radially inward from the interior surface. The actuator may include a diaphragm that bisects the second cavity into a first portion and a second portion. An outer periphery of the diaphragm may be coupled to an interior wall of the second cavity, and an interior periphery of the diaphragm may be coupled to an exterior surface of the outer collar. The body may also include a first passage that provides fluid communication with the first portion of the second cavity and a second passage that provides fluid communication with the second portion of the second cavity. Pneumatic pressure may be alternately supplied to the first portion of the second cavity via the first passage and the second portion of the second cavity via the second passage to alternately displace the diaphragm in opposing directions thereby oscillating the outer collar.

The plurality of cams may include a first plurality of cams disposed proximate a first end of the cam device and a second plurality of cams disposed proximate a second end of the cam device. The at least one engaging member may engage one of the first plurality of cams when the at least one engaging member is moved towards the first end of the cam device to cause the cam device to rotate in a first angular direction, and the at least one engaging member may engage one of the plurality of the second plurality of cams when the at least one engaging member is moved towards the second end of the cam device to cause the cam device to rotate in the first angular direction. Each cam of the plurality of cams may include an engagement surface operable contact the at least one engaging member. The engaging surface may include a slope to cause a rotation to the cam device as the at least one engaging member slides along the engagement surface. The first plurality of cams and the second plurality of cams may be rotationally offset from each other about the longitudinal axis. The apparatus may also include an advancement component. The advancement component may include a first engaging feature, and the lead screw may include a second engaging feature. The first engaging feature and the second engaging feature may matingly engage to cause the lead screw to translate longitudinally along the longitudinal axis when the lead screw is rotated. The first engaging feature may be a threaded portion, and the second engaging feature may be an outer threaded surface. The advancement component may include a slot, and the first engaging feature may be formed on an interior surface of the slot.

The housing may include a slot. The advancement component may be slideable within the slot between a first position in which the first engaging feature is engaged with the second engaging feature and a second position in which the first engaging feature is not engaged with the second engaging feature. The cam device may also include a central passage defining an interior wall and a protrusion extending inwardly from the interior wall. The cam device may include a longitudinally extending slot, and the cam device may be coupled to the lead screw by receipt of the protrusion into the longitudinally extending slot. The lead screw may be longitudinally slideable within a passage formed within the cam device and rotationally fixed within the cam device. The apparatus may also include a needle defining a lumen. The needle may be coupled to the body such that the lumen is in communication with the first opening.

The various aspects may also include one or more of the following features. A plunger may be coupled to an end of the lead screw. The plunger may be displaced through a cavity in response to the longitudinal displacement of the lead screw. The cavity may contain a material, and a portion of the material may be displaced in the cavity by the plunger.

The details of one or more implementations of the present disclosure are set forth in the accompanying drawings and the description below. Other features, objects, and advantages will be apparent from the description and drawings and from the claims.

DETAILED DESCRIPTION

Figure 1:
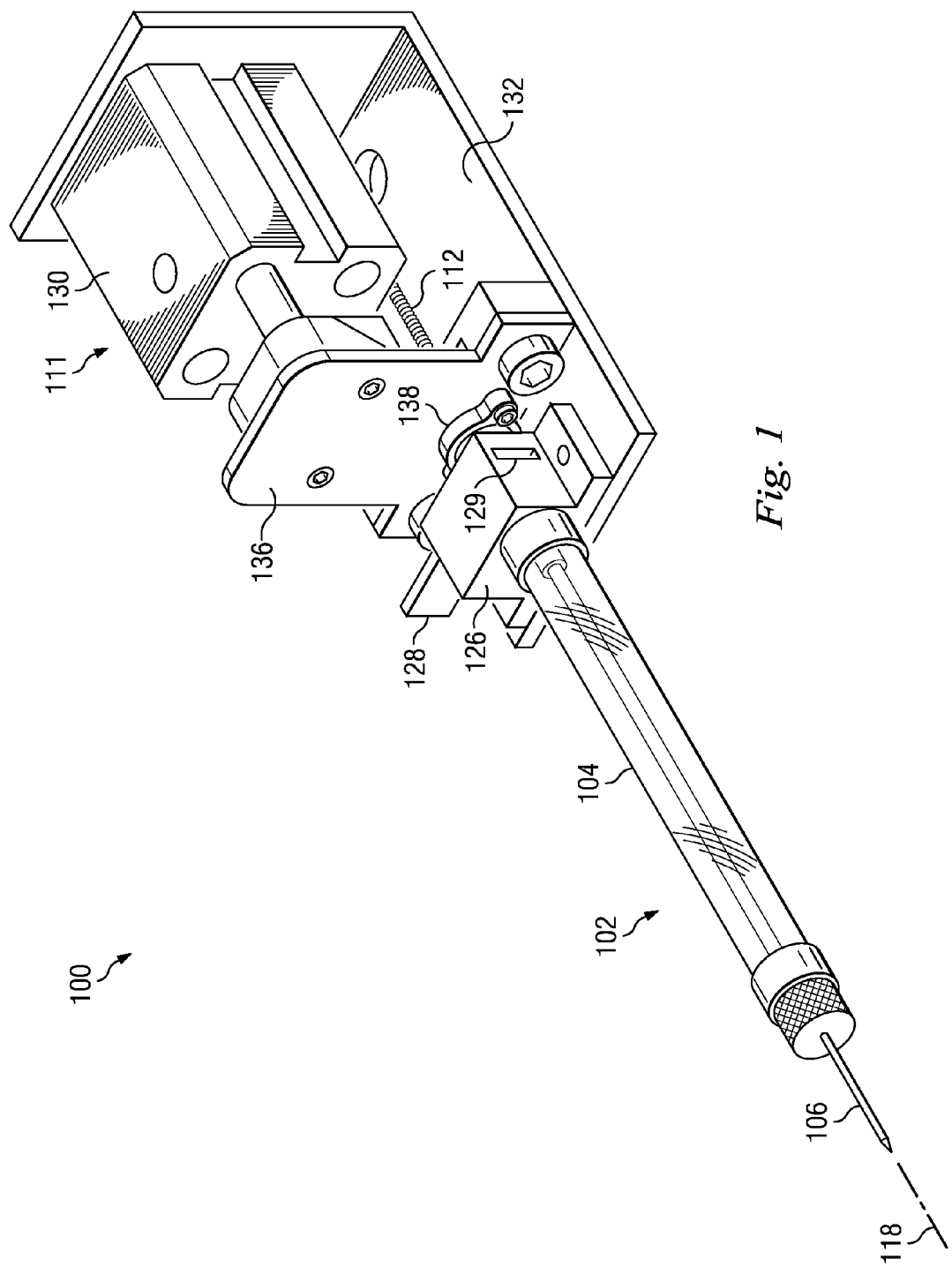
FIG. 1 is a perspective view of an example device for one of injecting or aspirating material.

For the purposes of promoting an understanding of the principles of the present disclosure, reference will now be made to the embodiments implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment implementation may be combined with the features, components, and/or steps described with respect to other embodiments implementations of the present disclosure.

The present disclosure describes devices, systems, and associated methods. The devices, systems, and methods described herein are made in the context of ophthalmic surgical procedures. However, use in ophthalmology is provided merely as an example and is not intended to be limiting. Thus, the devices, systems, and methods described herein may be applicable to numerous other fields and applications, which are intended to be encompassed by this disclosure.

In some instances, the devices, systems, and methods of the present disclosure may be utilized to deliver fluids to retinal and sub-retinal regions of a patient's eye. For example, the devices, systems, and methods described herein may be used to deliver materials such as anticoagulants, therapeutic drugs, anti-VEGF drugs, and/or any other fluids for being introduced into a patient's eye.

Figure 2:
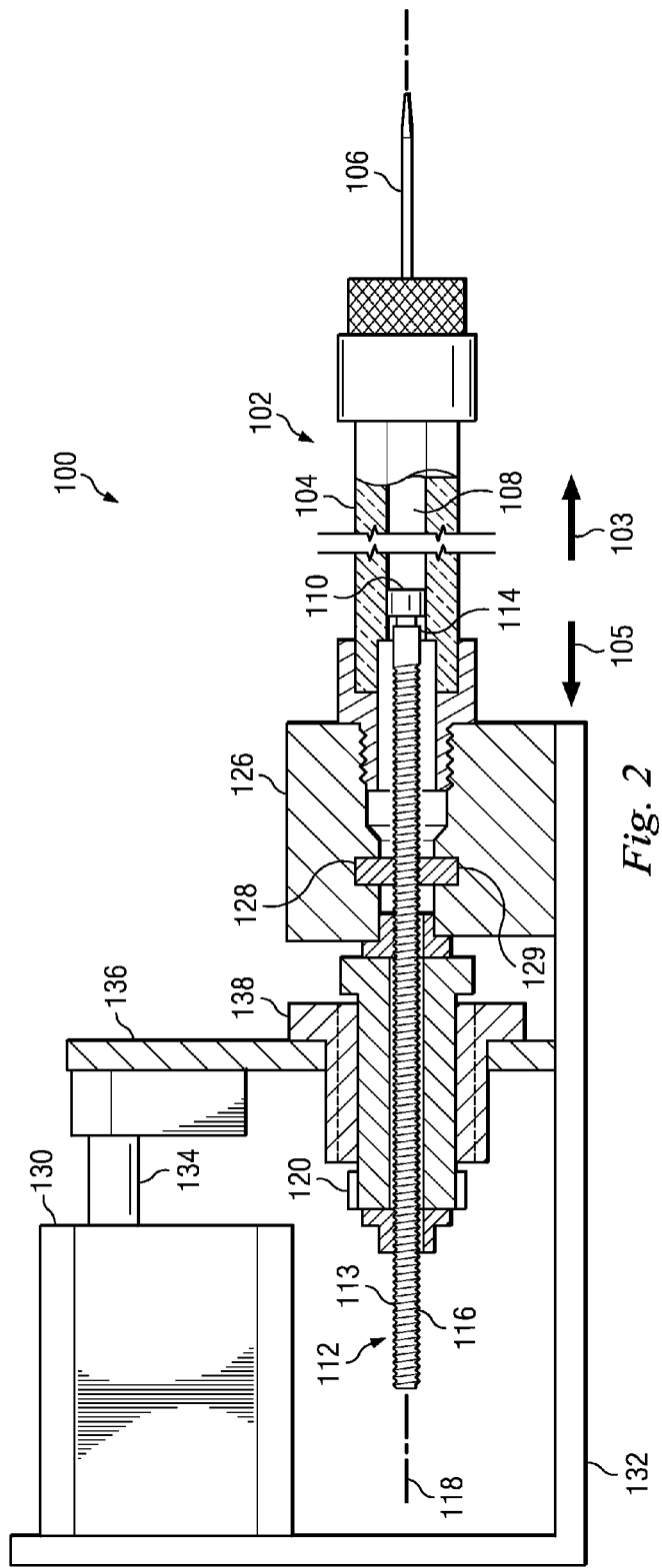
FIG. 2 is a partial cross-sectional view of the example device of FIG. 1.

FIGS. 1 and 2 show aspects of an example device 100, such as for use in an ophthalmic surgical procedure. As shown, the device 100 may include a syringe 102 including a body portion 104 and a needle 106 extending distally from the body portion 104. The body portion 104 defines a cavity 108 that is in communication with the lumen of the needle 106. The syringe 102 is coupled to an actuation system 111.

The device 100 may also include a housing 126 and a frame 132. Further, the actuation system 111 includes an actuator 130. In example shown, the frame 132 may provide a base onto which other portions of the device 100 are attached, directly or indirectly. For example, FIGS. 1 and 2 show the actuator 130 and the housing 126 attached to the frame 132. However, in other implementations, the device 100 may be configured differently, such as the example device 1500 shown in FIGS. 15 and 16, which is discussed in more detail below.

Referring again to FIG. 2, in some instances, the cavity 108 is adapted to receive a material that is to be dispensed from the syringe 102 through needle 106 during a procedure. For example, in some instances, the device 100 may be used to inject material into, on, or proximate to the eye. A plunger 110 may be positioned within the cavity 108. The plunger 110 may be translated distally towards the needle 106 to expel material within the cavity 108 out of the syringe 102 via the needle 106. In other instances, the cavity 108 may be utilized to receive a fluid during a surgical procedure. Thus, the plunger 110 may be moved proximally or away from the needle within the cavity 108 to draw material thereinto through the needle 106.

In some implementations, the actuation system 111 is operable to cause the device 100 to deliver material from the syringe in a controlled manner. In some implementations, the actuation system 111 is operable to aspirate material from the syringe 102 in a controlled manner. Particularly, the actuation system 111 is operable to control the displacement of the plunger 110 through the cavity 108 of the syringe 102. As shown in FIG. 2, the actuation system 111 may include a lead screw 112 having a first end 114 and a second end 116. A longitudinal axis 118 extends substantially parallel and coaxial with the cavity 108 in the main body 104 of the syringe 102. The lead screw 112 includes an outer threaded surface 113. The pitch of the outer threaded surface 113 may be any desired pitch. For example, the pitch of the outer threaded surface 113 may be selected based on a desired rate of advancement of the lead screw 112 and plunger 110 through the cavity 108 for a given amount of rotation of the lead screw 112. The first end 114 of the lead screw 112 may be coupled to the plunger 110. As discussed in greater detail below, as the lead screw 112 is rotated, the lead screw 112 may be advanced relative to the main body 104 in the direction of arrow 103, causing the plunger 110 to move through the cavity 108 in the direction of arrow 103.

In some instances, the first end 114 of the lead screw 112 is may be coupled to the plunger 110. Thus, in some implementations, as the lead screw 112 is moved relative to the syringe 102 in a direction corresponding to arrow 103, the plunger 110 is accordingly advanced through the cavity 108 in the direction of arrow 103. Similarly, in some implementations, as the lead screw 112 is moved in the direction of arrow 105, the plunger 110 is also moved through the cavity 108 in the direction of arrow 105. In some instances, the plunger 110 may be fixedly coupled to the first end 114 of the lead screw 112 such that the plunger 110 may rotate with the lead screw 112 as the plunger 110 moves through the cavity 108. In other instances, the plunger 110 may be rotatably coupled to the first end 114 of the lead screw 112 such that the plunger 110 and the lead screw 112 are allowed to rotate relative to each other. Thus, in some implementations, the plunger 110 may not rotate with the lead screw 112, or the plunger 110 may rotate to a lesser extent than the lead screw 112 as the plunger 110 is moved through the cavity 108. In still other implementations, the lead screw 112 may contact the plunger 110 but may not otherwise be coupled to the lead screw 112. Therefore, in such implementations, the plunger 110 is moveable with the lead screw 112 in the direction of arrow 103 but not in the direction of arrow 105.

The proximal portion 116 of the lead screw 112 is coupled to a cam device 120, such that rotation of the cam device 120 causes rotation of the lead screw 112. The cam device 120 may be positioned adjacent the housing 126 and may have a position along the longitudinal axis 118 that is fixed relative to the housing 126. Additionally, the cam device 120 is rotatable about longitudinal axis 118 relative to the housing 126.

As shown in FIGS. 5-6 and 9-10, the cam device 120 may include a passageway 121 for receiving the lead screw 112. The passageway 121 may define a protrusion or key 122. The key 122 may be sized and shaped to be received within a slot 124 that extends along the length of the lead screw 112. In some instances, the slot 124 may extend the entire length of the lead screw 112. In other instances, the slot 124 may extend along only a portion of the entire length of the lead screw 112. The key 122 transmits rotational movement of the cam device 120 to the lead screw 112 via the slot 124. Thus, engagement of the key 122 with the slot 124 allows the lead screw 112 to be rotated with the cam device 120. Further, engagement of the key 122 with the slot 124 also allows the lead screw 112 to translate longitudinally along axis 118 relative to the cam device 120 during rotation.

Figure 4:
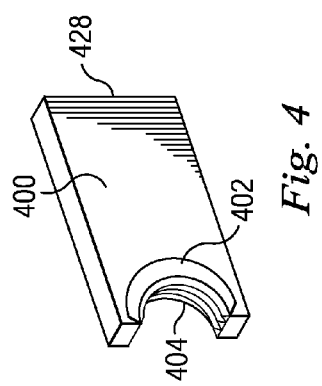
FIGS. 3 and 4 are show example advancement components according to some implementations.
Figure 3:
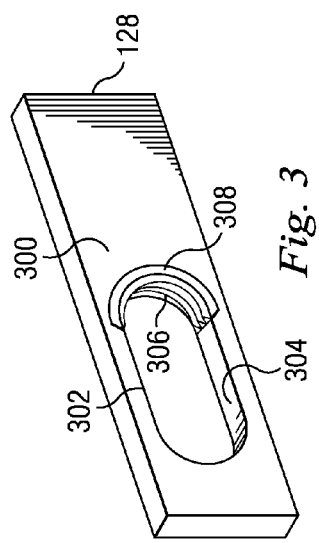

Referring to FIGS. 2-4, the device 100 may also include an advancement component 128 that is received within a slot 129 formed in the housing 126, and the advancement component 128 may be slideable within the slot 129. In some implementations, the advancement component 128 may be coupled to the housing 126. Thus, in some implementations, the advancement component 128 may be slideable within the slot 129 but may be prevented from being removable therefrom. In other instances, the advancement component 128 may be freely removable from the slot 129.

Referring to FIG. 3, the advancement component 128 may include a gripping portion 300 and a slot 302. The lead screw 112 may extend through the advancement component 128 when the advancement component 128 is received in the slot 129. An inner surface 304 of the slot 302 may include a threaded portion 306 having threads formed thereon. The threads of the threaded portion 306 may be configured to matingly engage the threads formed on the threaded surface 113 of the lead screw 112. In some implementations, the threaded portion 306 may extend along a semi-circular end of the slot 302. For example, the threaded portion 306 may extend approximately 180° along the end 308 of the slot 302. In other implementations, the threaded portion 306 may extend along more or less of the inner surface 304.

When the lead screw 112 is desired to advance through the cavity 108 of the syringe 102, a user may grip the gripping portion 300 and slide the advancement component 128 through the slot 129 such that the threaded portion 306 of the inner surface 304 engages the threaded surface 113 of the lead screw 112. Thus, as the lead screw 112 is rotated, the mating threaded surfaces cause the lead screw 112 to be advanced through the cavity 108 in the direction of arrow 103 (shown in FIG. 2). When advancement of the lead screw 112 is to be prevented, a user may retract the advancement component 128 so that the threaded portion 306 of the inner surface 304 is disengaged from the threaded surface 113 of the lead screw 112. In such a configuration, rotation of the lead screw 112 does not cause advancement of the lead screw 112 through the cavity 108. Thus, the lead screw 112 may be freely slideable within the cavity 108 in either of directions corresponding to arrows 103, 105.

Although the advancement component 128 is shown as a member having an elongated slot, the disclosure is not so limited. Consequently, the advancement component 128 may have other forms. For example, FIG. 4 shows an alternate implementation of the advancement component 428. As shown in FIG. 4, the advancement component 428 may include a gripping portion 400 and a semi-circular recess 402. An inner surface 404 of the recess 402 may be threaded for threadably engaging the threaded surface 113 of the lead screw 112 in a manner similar to that described above. However, the advancement member 428 may be removed from the recess 129 formed in the housing 126, as the advancement member 428 does not capture the lead screw 112. Thus, in some implementations, the advancement component 128 may be a half nut.

When the lead screw 112 and the advancement component 128 are not engaged, the lead screw 112 is freely slideable in the directions of arrows 103, 105. Further, the lead screw 112 may be freely slideable whether or not the lead screw 112 is being rotated. Thus, when disengaged, the lead screw 112 and plunger 110 may be retracted through the cavity 108 in a direction of arrow 105 (shown in FIG. 2). Sliding the lead screw 112 and plunger 110 in the direction of arrow 105 while the lead screw 112 is disengaged from the advancement component 128 may be used to load material, such as medicine or other desired materials, into the cavity 108. With the desired material is loaded into the cavity 108 the advancement member 128 may be engaged with the lead screw 112, which then allows the actuation system 111 to control the dispensing of the material from the syringe 102. Because of the precise control provided by the device 100 in dispensing materials therefrom, both in terms of volume and flow rate, there is less need to ensure that an exact amount of material needed for a particular procedure is loaded into the syringe 102. Rather, as long as enough material is loaded into the syringe 102, the actuation system 111 may be used to control the amount and/or rate of dispensation of the material.

While in some instances, engagement of the advancement component 128 with the lead screw 112 may cause the lead screw 112 to be advanced in the direction of arrow 103 by operation of the actuation system 111, in other instances, the lead screw 112 may be made to move in the direction of arrow 105. Thus, in some instances, the lead screw 112 may be made to move the plunger 110 through the cavity 108 in the direction of arrow 103 so as to expel material from the cavity 108 through needle 106. However, in other instances, the device 100 may include a lead screw 112 that may be made to move in the direction of arrow 105 so as to draw material into the cavity 108 of the syringe 102.

As indicated above, the rate at which the lead screw 112 is moved along the longitudinal axis 118 (e.g., the rate at which material is dispensed from or drawn into the cavity 108) may be defined by the rate at which lead screw 112 is rotated as well as the pitch of the threads 113 formed on the lead screw 112 and the threaded portion 306 of the advancement component 128. The device 100 provides for precise control of the amount of material expelled and/or aspirated as well as precise control of the rate at which the material is expelled and/or aspirated. Because of this precise control, the amount of material initially loaded into the syringe 102, such as when injecting material, is of less importance. That is, there is less need to ensure that an exact amount of material needed for a particular procedure is loaded into the syringe 102. Rather, as long as enough material is loaded into the syringe, the actuation system 111 will control the dispensing of the material in a manner that provides the desired amount of material for the procedure.

Referring again to FIGS. 1 and 2, the actuator 130 may include a piston 134 coupled to an outer collar 138. In some instances, the piston 134 may be coupled to the outer collar 138 via a coupling member 136. In some instances, the coupling member 136 may be a plate. The interface between actuator 130 and the outer collar 138 shown in FIGS. 1 and 2 (i.e., via piston 134 and plate 136) is provided merely as an example and is not intended to be limiting in any way. Rather, the outer collar 138 may be coupled to the actuator 130 in any manner such that the actuator 130 imparts oscillatory motion to the outer collar 138.

In some instances, the actuator 130 may be a pneumatic actuator. Particularly, the actuator 130 may include a diaphragm that is pneumatically-actuated in at least one direction. In other instances, the actuator 130 may be a hydraulic actuator. Thus, in some instances, the actuator 130 may be a pneumatically or hydraulically actuated piston. In still other implementations, the actuator 130 may be an electric actuator. In some instances, the actuator 130 is a dual-action mechanism. An example dual-action mechanism may be a diaphragm disposed in a pneumatic chamber to which pneumatic pressure may be alternately applied to opposing sides of the diaphragm. In other instances, the actuator 130 may be a single-action mechanism. A biasing element, such as a spring, may be utilized in a single-action mechanism to provide a return force against the actuator force to return an oscillating member thereof back to an initial position. Still further, the actuator 130 may be any suitable actuator operable to generate an oscillating action. For example, the actuator 130 may be a solenoid, an electro-magnetic actuator, a piezo-electric actuator, or other suitable actuator.

Figure 5:
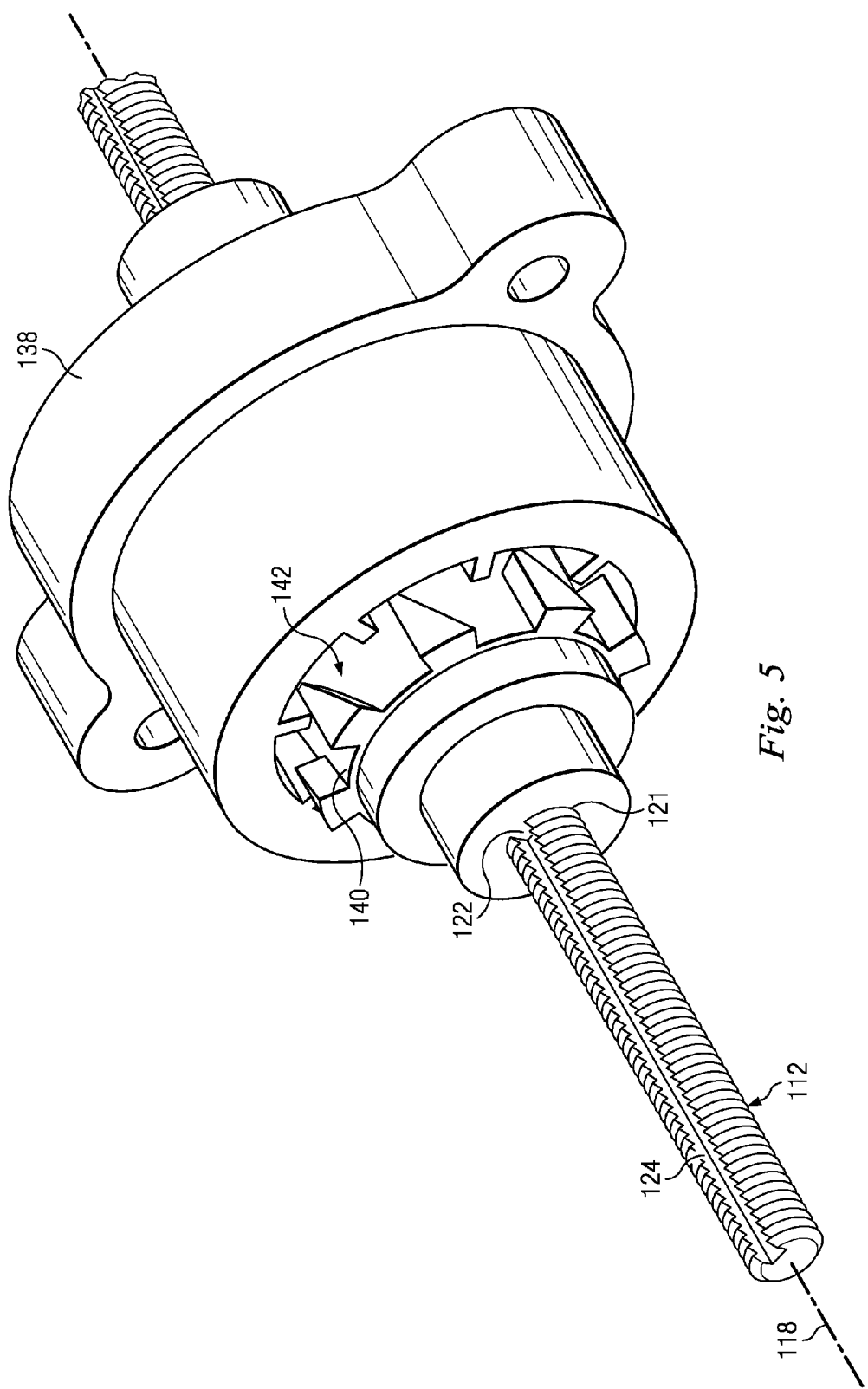
FIGS. 5 and 6 are perspective views of a portion of an example actuator mechanism of device shown in FIGS. 1 and 2.
Figure 6:
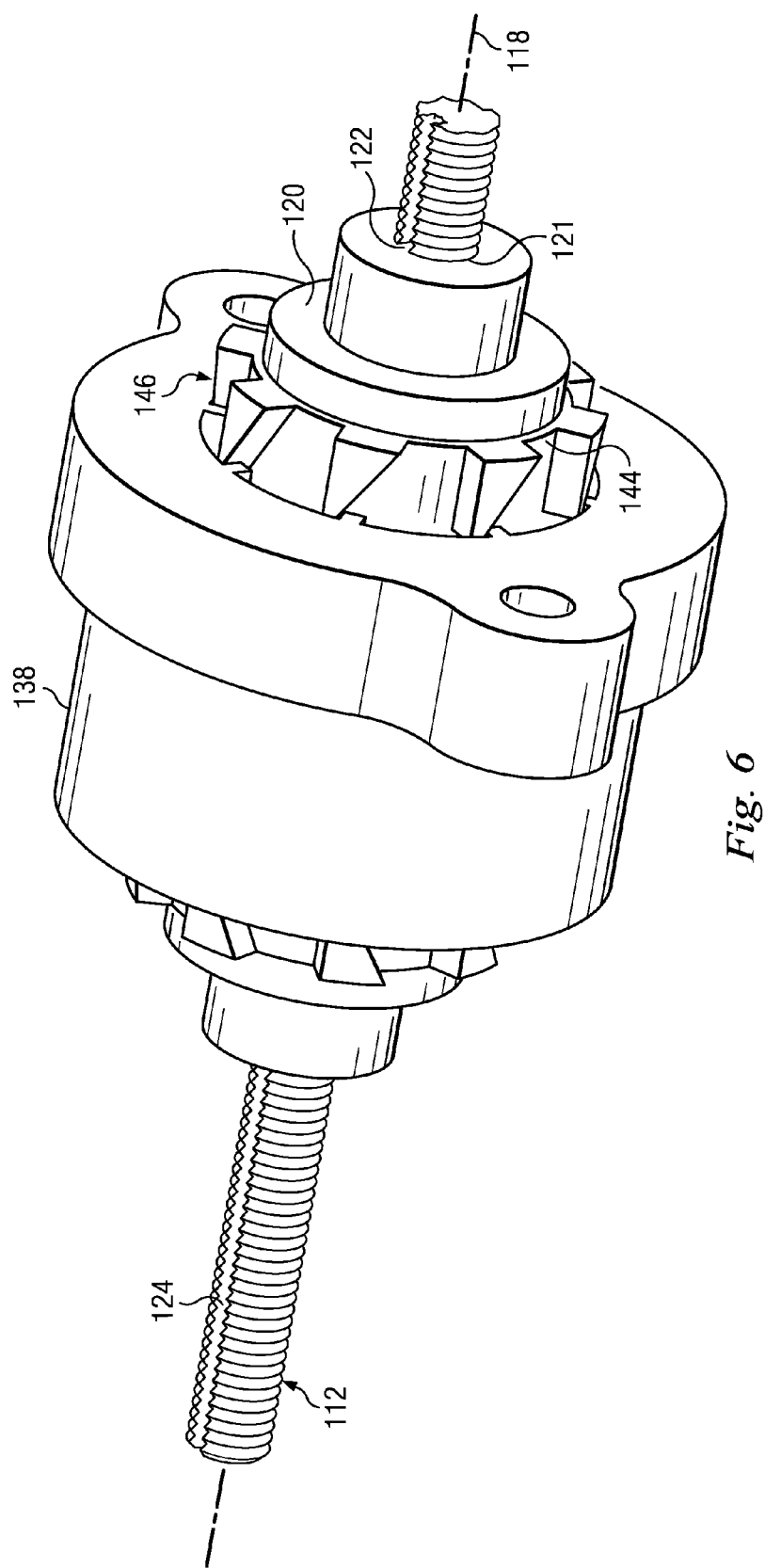

FIGS. 5 and 6 are perspective views showing an example assembly of the lead screw 112, cam device 120, and outer collar 138 according to some implementations. As shown, the cam device 120 receives the lead screw 112 within passageway 121 such that the key 122 is received into and engages slot 124 of the lead screw 112. Further, the outer collar 138 is positioned circumjacent the cam device 120.

Referring to FIGS. 7-10, the cam device 120 may be a generally cylindrical member having a first plurality of cams 142 disposed proximate a first end 140 and a second plurality of cams 146 disposed proximate a second end 144. The first plurality of cams 142 and the second plurality of cams 146 may be formed on an outer surface 145 of the cam device 120. The first plurality of cams 142 are angularly offset from the second plurality of cams 146. That is, the cams 141 of the first plurality of cams 142 do not align longitudinally with the cams 141 of the second plurality of cams 146. While the first plurality of cams 142 and the second plurality of cams 146 are each shown as including eight cams 141, the plurality of cams 142, 146 may include any number of cams 141.

Figure 8:
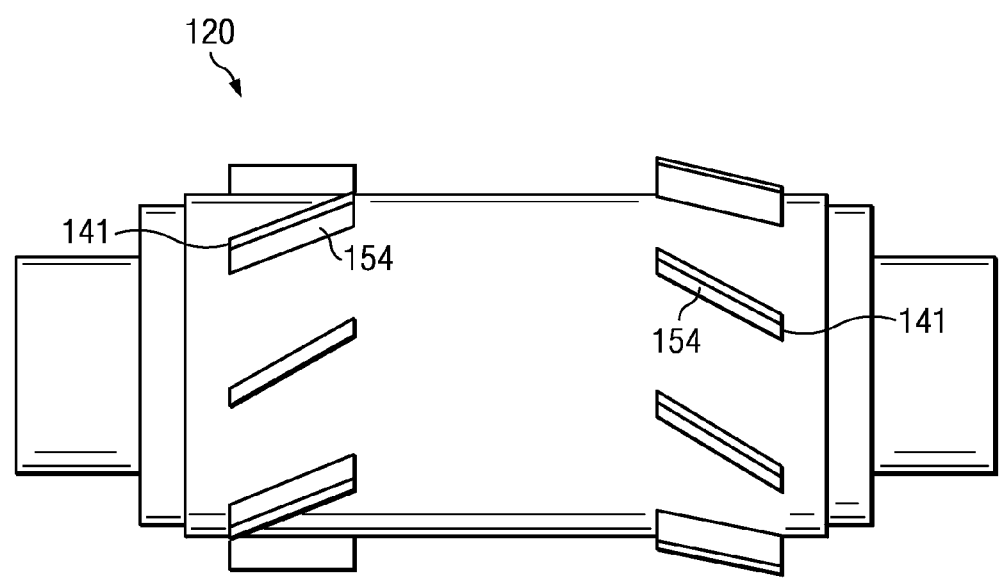
FIG. 8 shows another example cam device.
Figure 9:
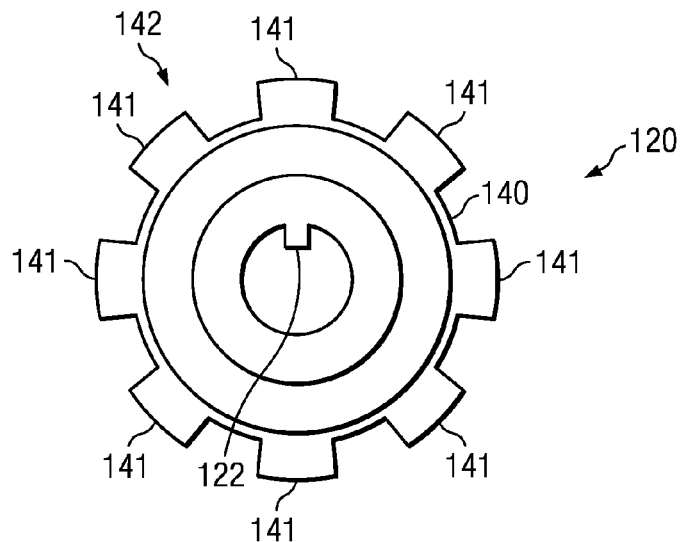
FIG. 9 is an end view of a first end of the example cam device of FIG. 7.
Figure 10:
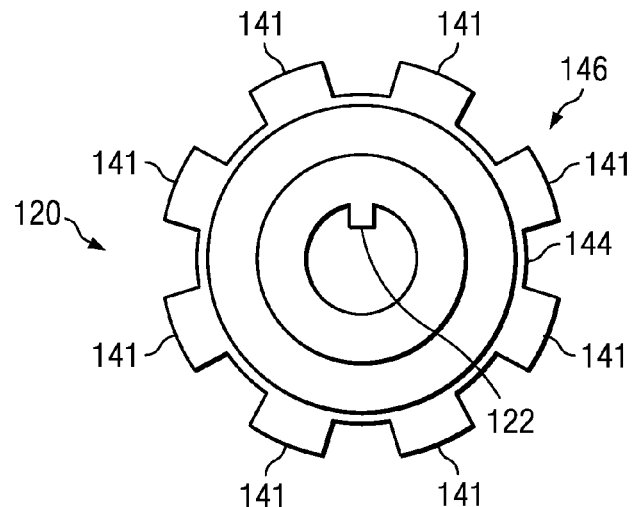
FIG. 10 is an end view of a second end of the example cam device of FIG. 7.

In some instances, each cam 141 of the plurality of cams 142, 146 may have a generally triangular shape. Particularly, in some instances, the cams 141 may have a generally right triangular shape. Further, each cam 141 may include a sloped side 148, a longitudinal side 150, and a base side 152. The sloped side 148 defines an engagement surface 154. However, in other instances, the cams 141 may have any desired shape. For example, as shown in FIG. 8, in some instances, the cams 141 may be in the form of a vane disposed at an angle relative to the longitudinal axis 118. Further, in some implementations, the engagement surface 154 may be angled, arcuate, curved, or otherwise configured to cause rotation of the cam device 120 through interactions with the mechanism 138

The cams 141 of the first plurality of cams 142 are configured such that the base sides 152 are disposed adjacent first end 140. The cams 141 of the second plurality of cams 146 are similarly arranged such that the base sides 152 are arranged adjacent the second end 144. Additionally, the engagement surface 154 of each cam 141 is arranged on a common side, as shown, for example, in FIG. 7.

Figure 11:
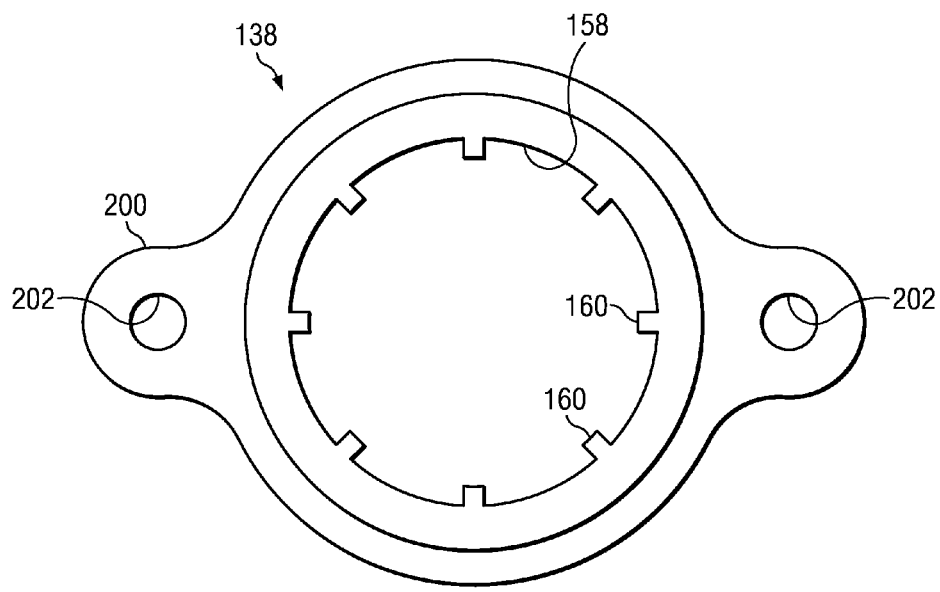
FIG. 11 is an end view of an example collar of the example actuator mechanism of FIGS. 5 and 6.

Referring to FIG. 11, the outer collar 138 includes an interior cavity 156 and an interior surface 158. The interior cavity 156 is adapted to receive the cam device 120. A plurality of engaging members 160 is disposed on the interior surface 158. In some instances, the plurality of engaging members 160 may be integrally formed on the interior surface 158. The plurality of engaging members 160 radially extend into the interior cavity 156. Although the outer collar 138 is shown as included a plurality of engaging member 160, the outer collar 138 may include as few as a single engaging member 160 to engage the cams 141 of the cam device 120.

In some instances, the outer collar 138 may also include a flange 200. The flange 200 may include openings 202 formed therein. The openings 202 accept fasteners for coupling the outer collar 138 to the plate 136, although, as mentioned above, the outer collar 138 may be coupled to the actuator 130 in other ways. Leading edges of the engaging members 160 are adapted to contact and slide along the engagement surface 154 of the cams 141.

Figure 12:
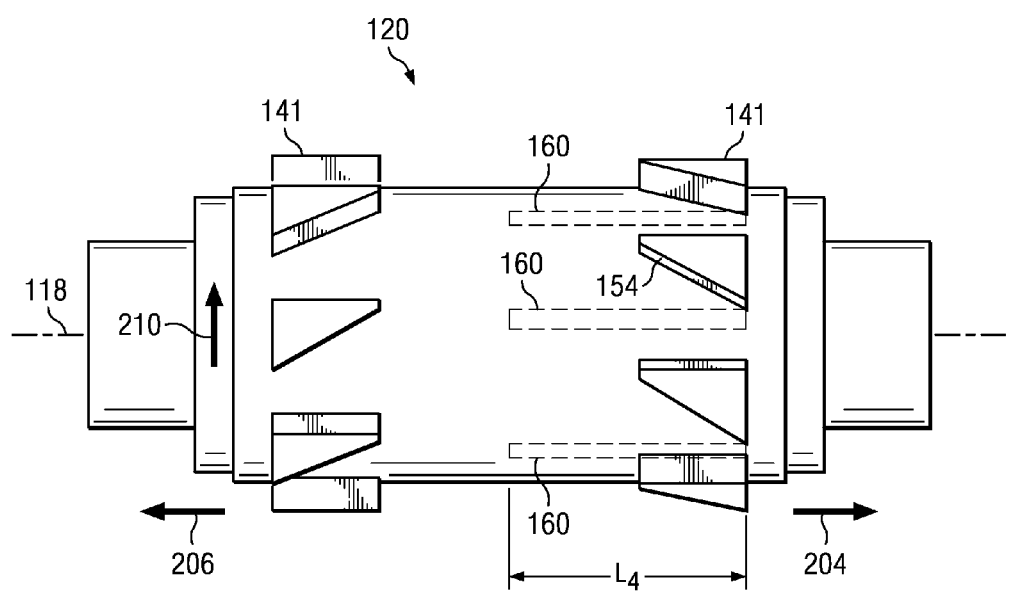
FIG. 12 is a side view of the of an example cam device showing interaction of engaging members with cams of the cam device in a first position.
Figure 13:
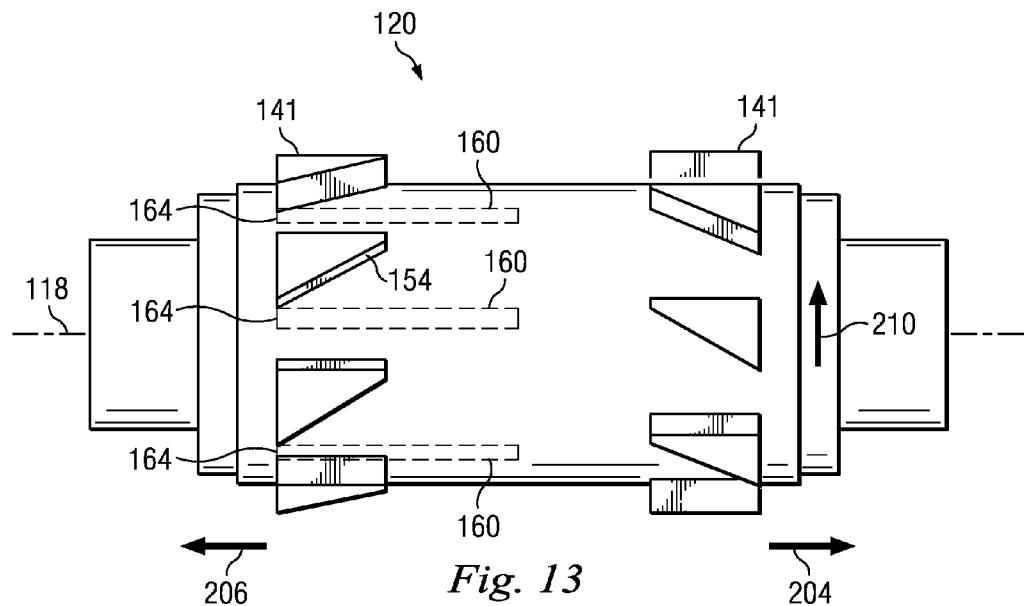
FIG. 13 is a side view of the of the example cam device of FIG. 12 showing interaction of the engaging members with cams of the cam device in a second position.
Figure 14:
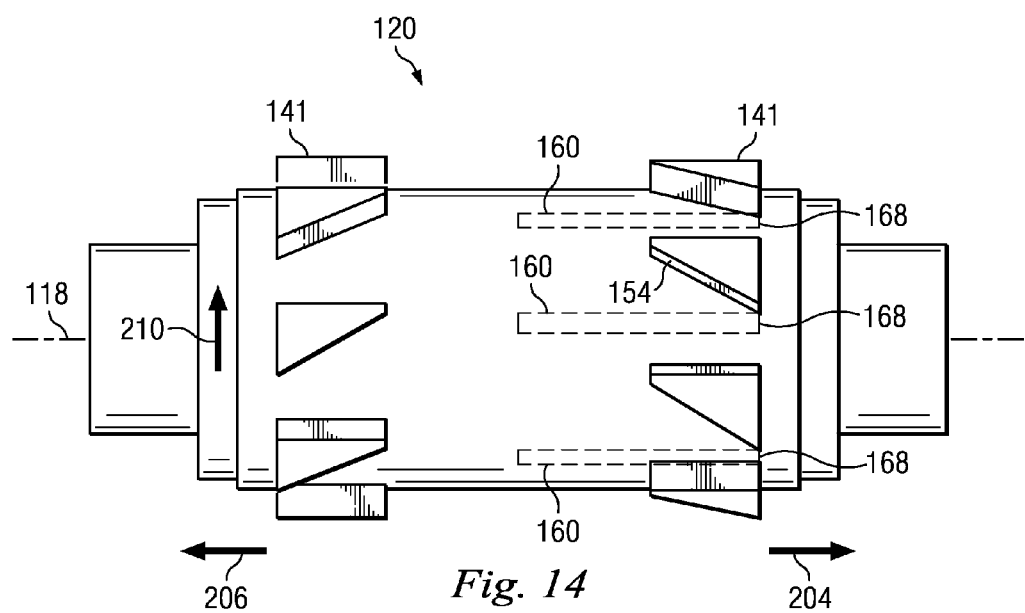
FIG. 14 is a side view of the of the example cam device of FIG. 12 showing interaction of the engaging members with cams of the cam device in a first position.

During operation, the actuator 130 oscillates the outer collar 138. The oscillation of the outer collar 138 relative to the cam device 120 causes the cam device 120 to rotate about longitudinal axis 118 in a single direction. FIGS. 12-14 illustrate the oscillatory movement of the outer collar 138 and the resulting rotation experienced by the cam device 120. In FIG. 12, the engaging members 160 (shown with dotted lines) are shifted towards the second end 144 (i.e., in the direction of arrow 204). In FIG. 13, the engaging members 160 are shifted towards the first end 140 (i.e., in the direction of arrow 206) as the outer collar 138 is moved by the actuator 130. A first edge 164 of the engaging members 160 contacts the engagement surface 154 of the cams 141. Because the outer collar 138 is prevented from rotation during longitudinal displacement, the cam device 120 is rotated as the first edges 164 slide across the engagement surfaces 154 of the cams 141 of the first plurality of cams 142. As the outer collar 138 is shifted back towards the second end 144 of the cam device 120 in the direction of arrow 204 (shown in FIG. 14), second edges 168 of the engaging members 160 contact the engagement surfaces 154 of the cams 141 of the second plurality of cams 146. This also causes the cam device 120 to rotate in the direction of arrow 210. Thus, as the outer collar 138 is oscillated, the cam device 120 is rotated in a single direction. It is understood that the cams 141 may be arranged such that the cam device 120 is made to rotate in a direction opposite to arrow 210. Further, rotation of the cam device 120 may be increased or decreased by increasing or decreasing the rate of oscillation of the oscillator 130.

The amount by which the cam device 120 may be made to rotate for each displacement of the engaging member(s) 160 may be defined by the number of cams situated around the circumference on each end of the cam device 120. For example, as the number of cams 141 increases, the smaller the amount of rotation for each displacement of the engaging member(s) 160. On the other hand, as the number of cams 141 decreases, a larger amount of rotation of the cam device 120 results for each displacement. A slope of the engagement surface 154 of the cams 141 can be interrelated with the number of cams 141 to achieve a desired incremental rotation of the cam device 120 per oscillation of the engaging member(s) 160.

Figure 7:
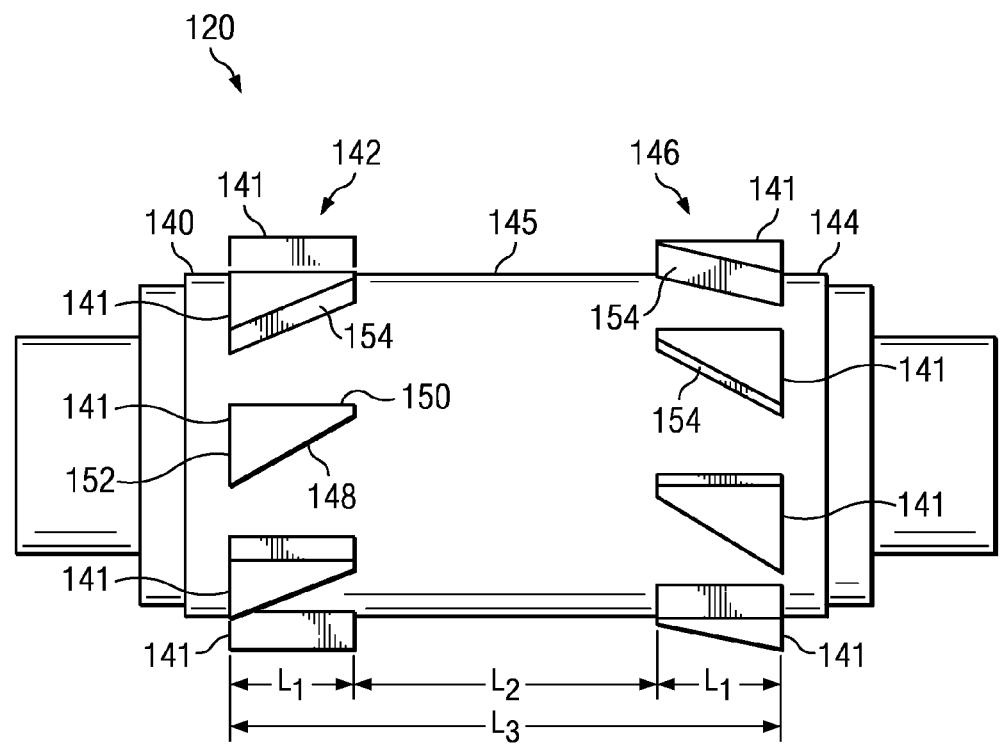
FIG. 7 is a side view of an example cam device.

As shown in FIG. 7, each cam 141 in the first plurality of cams 142 and the second plurality of cams 146 may have a longitudinal length of L1. A longitudinal length, L2, may extend between inboard edges of the cams 141. Referring to FIG. 12, the engaging members 160 are shown having a length L4. The length L4 of the engaging members 160 may be any length less than L1+L2. As the length L4 of the engaging members 160 approaches L1+L2, the smaller the stroke or longitudinal movement of the engaging members 160 that is required to rotate the cam device 120. Accordingly, as the length L4 approaches L1+L2, the device 100 becomes more efficient because a smaller movement of the outer collar 138 is required to cause the cam device 120 to rotate. As a result, the device 100 may be made more responsive as a result of the smaller stroke of the outer collar 138 needed to rotate the cam device 120. However, the length L4 of the engaging members 160 may be any desired length to permit rotation of the cam device 120.

As explained above, the lead screw 112 is made to rotate with the cam device 120 due to engagement of the key 122 and slot 124. With the threaded portion 306 of the advancement component 128 engaged with the threaded surface 113 of the lead screw 112, as the cam device 120 is rotated by the outer collar 138, the lead screw 112 is translated along longitudinal axis 118 so as to displace the plunger 110 in the cavity 108. In some implementations, the plunger 110 may be made to move in the direction of arrow 103, such as to cause material to be expelled from the cavity 108. In other implementations, the plunger 110 may be made to move in the direction of arrow 105 to cause material to be drawn into the cavity 108.

Although the engaging members 160 are shown as being disposed on the interior surface of the outer collar 138, the scope of the disclosure is not so limited. Rather, in some instances, the outer collar 138 may be replaced by a member oscillatable relative to the cam device 120 but otherwise not necessarily forming a ring circumjacent thereto. The member may include one or more engaging members 160 for engaging the cams 141 of the cam device 120.

As explained above, the amount of advancement associated with rotation of the lead screw 112 may be dependent on the pitch of the threads formed on the threaded outer surface 113 of lead screw 112 and the corresponding threads formed on the threaded portion 306 of the advancement component 128. In some instances, the thread pitch of the threaded outer surface 113 and the threaded portion 306 may be between about 0.1 mm to 1.0 mm and, particularly, in some implementations approximately 0.2 mm to 0.6 mm. As the thread pitch is decreased, the device 100 is operable to precisely generate correspondingly smaller increments of motion because each rotation of the lead screw 112 translates into a smaller amount of linear translation of the lead screw 112 and, therefore, the plunger 110. In a similar manner, as explained above, as the number of cams 141 is increased, the device 100 is operable to precisely produce increasingly smaller increments of movement of the lead screw 112 and plunger 110. As a result, a smaller amount of rotation of the lead screw 112 is produced. Accordingly, the thread pitch associated with the lead screw 112 and the advancement component 128 and/or the number of cams 141 may be selected to define a desired resolution (i.e., an amount of material expelled from or aspirated into the syringe 102 per stroke of the outer collar 138) of the device 100.

Still further, a cross-sectional size of the cavity 108 (e.g., a diameter of the cavity 108 where the cavity 108 has a cylindrical profile) may also be selected to control an amount of material expelled from or aspirated into the syringe 102. As the size of the cavity 108 is decreased, a smaller amount of material is expelled or aspirated for a given displacement of the plunger 110. Conversely, as the cross-sectional size of the cavity 108 is increased, an increased amount of material is expelled or aspirated for a given displacement of the plunger 108.

In some implementations, the device 100 is operable to control the linear displacement of the plunger 110 in increments as small as 0.0005 inches or approximately 0.0127 mm. Also, according to some implementations, the resolution of the device 100 may be within the range of 0.02 microliters to 1.0 microliters. According to other implementations, the resolution may be less than 0.02 microliters or greater than 1.0 microliters. In still other implementations, the resolution of the device 100 may be 0.025 microliters.

In addition to precisely controlling the amount of material dispensed from the syringe 102, the device 100 may also control the flow rate at which material is dispensed from the syringe 102. For example, the flow rate may be controlled by adjusting the rate of oscillation of the outer collar 138. For a given device 100, the higher the rate of oscillation, the higher the rate of rotation of the cam device 120, and, hence, the faster the rate of linear displacement of the plunger 110 through the cavity 108. Conversely, the lower the rate of oscillation, the lower the rate of rotation of the cam device 120, and, accordingly, the lower the rate of linear displacement of the plunger 110 through the cavity 108. Thus, by controlling the speed of oscillation of the outer collar 138, the device 100 may be used to control the flow rate of the material expelled from or aspirated into the syringe 102. Because actuator 130 controls the oscillation of the outer collar 138, the speed at which the actuator 130 is driven may be used to control the rate at which material is expelled from or aspirated into the syringe 102.

In some instances, a specific flow rate may be achieved by determining the volume of material to be dispensed per stroke of the outer collar 138 (which can be determined, for example, by the shape of the engagement surfaces 156, the thread pitch associated with the lead screw 112 and advancement component 128, and the profile of the cavity 108 of the syringe 102) and actuating the actuator 130 to produce a desired oscillation rate of the outer collar 138 (e.g., a number of oscillations per unit of time) to achieve the desired flow rate. In some instances, the device 100 may be operated to generate a flow of material by rapidly dispensing multiple discrete micro-volumes of material. In other implementations, the device 100 may be used to generate a flow of material into the syringe 102 in a similar manner. The high frequency concatenation of micro-volumes may create a smooth flow of material with high volume accuracy and high flow rate accuracy. Accordingly, calculation of the appropriate actuation pattern for a particular flow rate can be determined based on the dispensed micro-volume of material for each oscillation of the outer collar 138.

For example, if the device 100 dispenses 0.0005 ml of material (e.g., a fluid) with each stroke of the outer collar 138, then the device 100 will dispense (or aspirate) 0.001 ml of material for each full oscillation of the outer collar 138 (i.e., translation of the outer collar 138 in the direction of arrow 103 and then back in the direction of arrow 105). Accordingly, if it is desired to have 0.01 ml of material dispensed per second, then the actuator 130 can be adjusted to oscillate the frame at 10 full oscillations per second. Similarly, if it is desired to have 0.1 ml of material dispensed per second, then the actuator 130 can be adjusted to oscillate the outer collar 138 at 100 oscillations per second. In some instances, oscillation of actuator 130 may be controlled to drive oscillation of the outer collar 138 at a rate corresponding to a desired flow rate of material into or out of the syringe 102. Thus, a desired flow rate for a device 100 may be determined or selected based on, for example, an oscillation rate of the actuator 130, the shape of the engagement surfaces 156, thread pitch associated with the lead screw 112 and advancement component 128, and the profile of the cavity 108.

Figure 15:
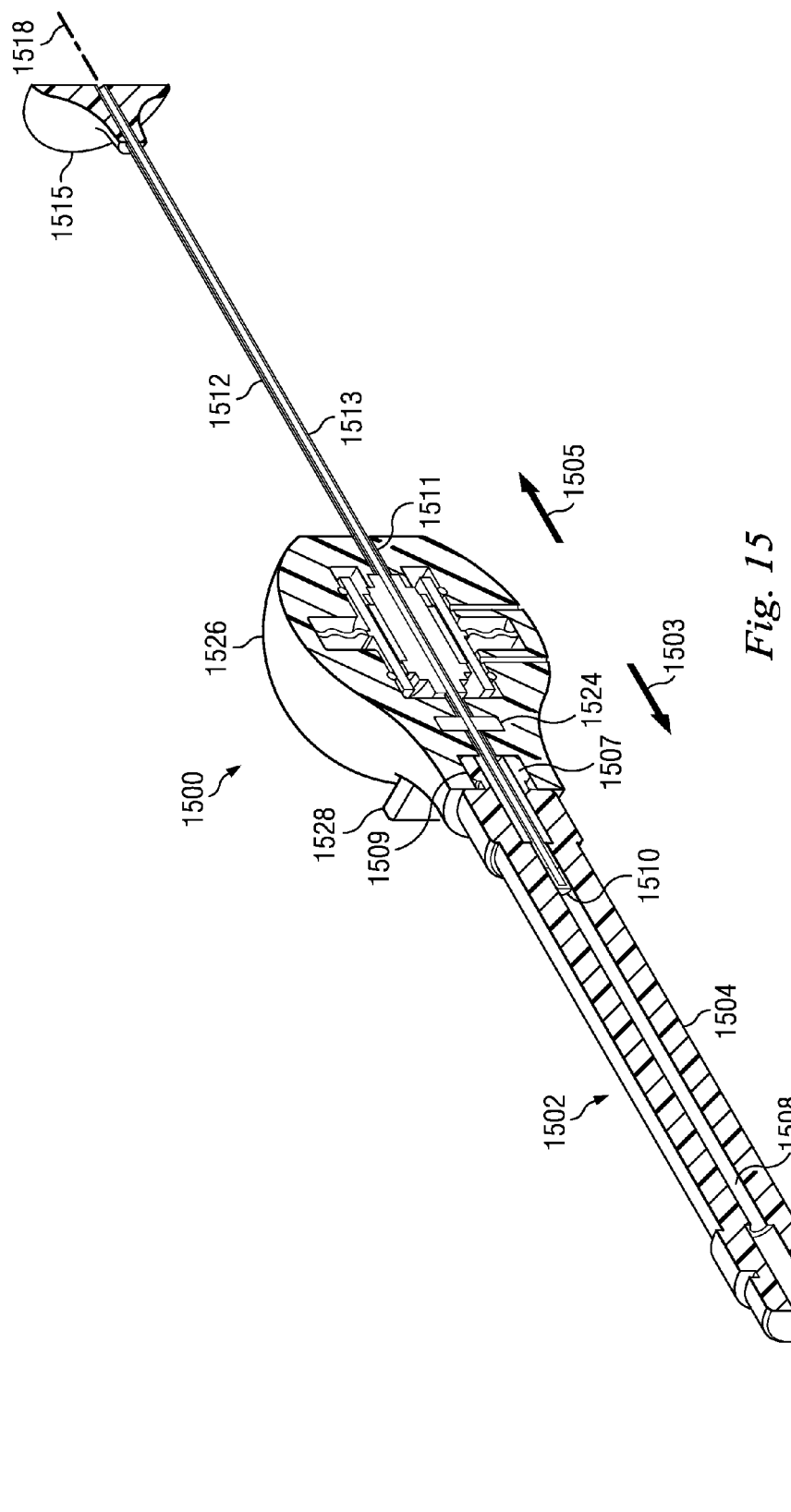
FIGS. 15 and 16 show another example device for one of injecting or aspirating material.
Figure 16:
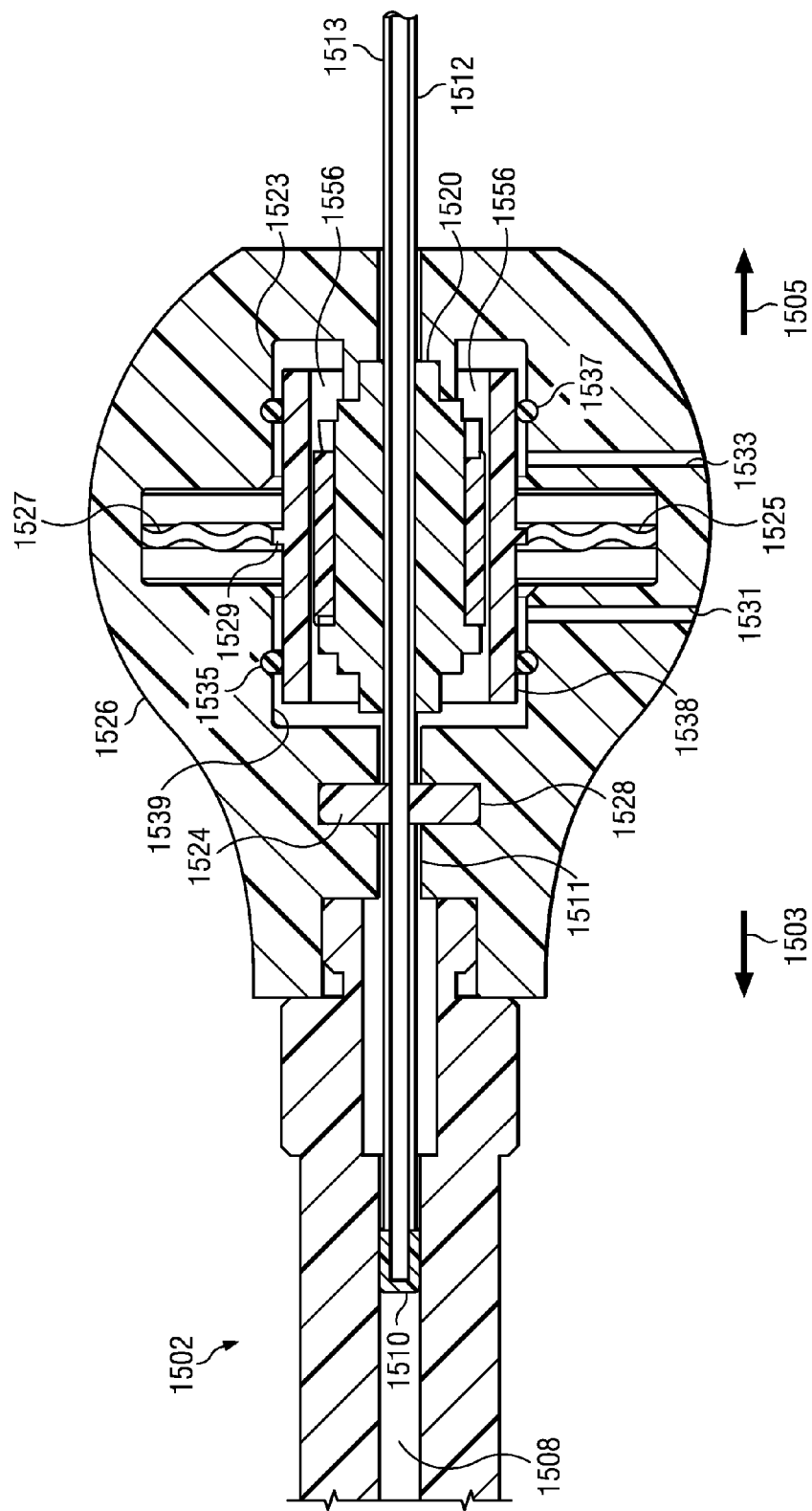

FIGS. 15 and 16 show another example device for at least one of injection or aspiration. FIG. 15 is a sectioned view of the example device 1500 taken along a plane passing through longitudinal axis 1518. The device 1500 includes a housing 1526 coupled to a syringe 1502. In some instances, the syringe 1502 may be removable. Thus, a protrusion 1507 of the syringe 1502 may be received into a receptacle 1509 formed in the housing 1526. A central passage 1511 is formed through the housing 1526. The central passage 1511 may be formed along the longitudinal 1518. The syringe 1502 may include a body portion 1504 that defines a cavity 1508. The central passage 1511 and the cavity 1508 may be aligned.

A lead screw 1512 may extend through the central passage 1511 and the cavity 1508. Similar to the lead screw 112, the lead screw 1512 may include an outer threaded surface 1513. A plunger 1510 may be disposed in the cavity 1508. Further, the plunger 1510 may be coupled to the lead screw 1512 in a manner described above with respect to the lead screw 112 and the plunger 110. The device 1500 may also include a handle 1515 attached at an end of the lead screw 1512, and a needle 1506 may be coupled to an end of the syringe 1502. A lumen of the needle 1506 may be in communication with the passage 1508 and an exterior of the device 1500.

The device 1500 may also include an advancement component 1528, which may be similar to the advancement component 128. Thus, the advancement component 1528 is moveable within a slot 1524 so as to engage the lead screw 1512 in a first position and not to engage the lead screw 1512 in a second position. Further, interaction of the advancement component 1528 with the outer threaded surface 1513 has functionality similar to that described above with respect to the advancement component 128 and the lead screw 112. As such, a further explanation is omitted.

Referring to FIG. 16, the housing 1526 includes a cavity 1523. A collar 1538 may be disposed within the cavity 1523. Also, a diaphragm 1525 may also be disposed in the cavity 1523. The diaphragm 1525 may be coupled to the housing 1526 at an outer periphery 1527 and to collar 1538 at an inner periphery 1529. Passages 1531 and 1533 extend through the housing 1526 and communicate with the cavity 1523. The passages 1531, 1533 are disposed on opposing sides of the diaphragm 1525. Seals 1535, 1537 may also be disposed in the cavity 1523 between the collar 1538 and an interior wall 1539 of the housing 1526. The seals 1535, 1537 provide a seal to maintain a pneumatic pressure within the cavity 1523 introduced into the cavity 1523 via the passages 1531, 1533. A cam device 1520 is also disposed in the cavity 1523 and is operable coupled to the lead screw 1512. For example, the cam device 1520 and the lead screw 1512 may be engaged via a slot and key arrangement similar to the slot 124 and key 122 arrangement described above.

The collar 1538 may be similar to the outer collar 138 and may operate similarly thereto. Also, the cam device 1520 may be similar to the cam device 120 and operate similarly thereto. For example, the cam device 1520 may include a plurality of cams, such as the cams 141 described above, and the collar 1538 may include a plurality of engagement members, such as the engagement members 160 described above.

In operation, fluidic pressure may be alternatingly supplied through the passages 1531, 1533. Thus, fluidic pressure may be applied alternately to opposite sides of the diaphragm 1525. The alternating fluidic pressure causes the diaphragm 1525 to be alternately displaced in the directions of arrows 1503 and 1505, thereby oscillating the collar 1538. Thus, the diaphragm 1525 is operable as an actuator to oscillate the collar 1538. The cam device 120 may have a longitudinally fixed position but freely rotatable within the cavity 1523 and within a cavity 1556 of the collar 1538. As a result, the cam device 1520 is rotated in the same direction for movement of the collar 1538 in both the direction of arrows 1503, 1505. The lead screw 1512 is similarly rotated. Engagement of the advancement component 1528 with the lead screw 1512 causes the lead screw to move longitudinally within the housing 1526 and the cavity 1508. As described above, the lead screw 1512 may be made to move in the direction of arrow 1503 so as to cause material to be expelled from the syringe through the needle 1506. Alternately, the lead screw 1512 may be made move in the direction of arrow 1505 so as to aspirate material into the syringe 1502 via the needle 1506.

When the advancement component 1528 is disengaged from the lead screw 1512, the lead screw 1512 is freely moveable longitudinally. For example, a user may use the handle 1515 to displace the lead screw 1512 in either of the directions of arrows 1503, 1505. Thus, in such a configuration, the lead screw 1512 may be used to draw material, such as a medicament, into the cavity 1508 prior to use.

Figure 17:
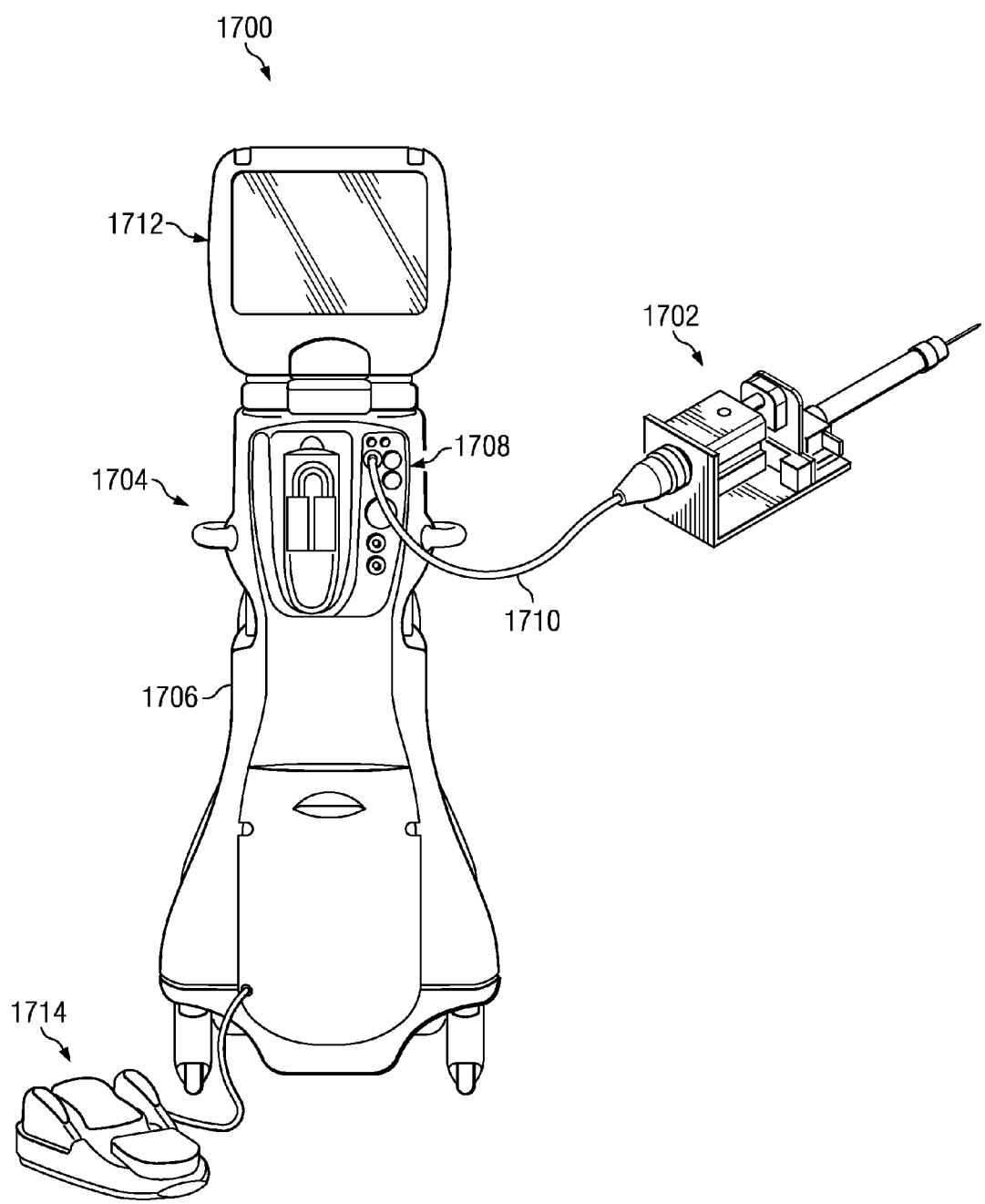
FIG. 17 shows an example ophthalmic surgical system.

FIG. 17 shows an example arrangement 1700. In particular, the arrangement 1700 may include an ophthalmic device 1702, which may be similar to devices 100 or 1500, discussed above. In some instances, the device 1700 may be used to inject a material, such as a medicine, into a patient's eye. In other implementations, the device 1700 may be used to aspirate materials from the patent's eye.

As shown, the device 1702 is connected to a surgical console 1704. The surgical console 1704 may be configured to operate the device 1702 to control a volume and/or flow rate of material dispensed therefrom or aspirated thereinto. In some instances, the surgical console 1704 may include features, connections, and interfaces similar to those provided by the Constellation® Vision System produced by Alcon Laboratories, Inc., of 6201 South Freeway, Fort Worth, Tex. As shown, the surgical console 1704 may include a cart base 1706 that provides portability to the surgical console 1704. The surgical console 1704 may also include a connection panel 1708 to provide an interface between the device 1702 and the surgical console 1704. A connector 1710 may be used to couple the device 1702 to the connection panel 1708.

Connectivity provided by the connector 1710 may be dependent upon the type of actuator included in the device 1702. For example, the connector 1710 may include one or more wires, one or more cables, one or more tubes, or other connectors, or the connector 1710 may include any combination of one or more wires, cables, tubes, and/or other connectors. For example, where the actuator is a pneumatic actuator, the connector 1710 may include one or more tubes for transmitting pneumatic pressure to and/or from the actuator. In other instances, the actuator may be electric. As such, the connector 1710 may include one or more wires or cables, for example, to transmit electrical power and/or control signals to the actuator from the surgical console 1704.

As noted above, the surgical console 1704 may be configured to drive the actuator of the device 1702 in order to control a volume and/or flow rate of material dispensed from or aspirated into the device 1702. Consequently, the surgical console 1704 may include one or more processors with associated memory that may be programmed, for example, to control the actuator so as to achieve the desired volume and/or flow rate. The processor(s) may take into account factors such as the desired volume, desired flow rate, the number of cams, thread pitch associated with the lead screw, and a profile of the cavity of the dispenser. The processor(s) may also utilize other information associated with one or more other factors. In some instances, a user may select a desired volume and/or desired flow. Further, in some instances, the user may select or input information regarding the parameters of the arrangement 1700. In other instances, information regarding the device 1702 may be stored in memory carried by the device 1702 that is readable by the surgical console 1704 such that, when the device 1702 is connected to the surgical console 1704, the information can be read and utilized by the surgical console 1704.

The surgical console 1704 may also include a display 1712. In some instances, a user may utilize the display 1712 to input or select desired information associated with the arrangement 1700, such as the surgical console 1704 and/or the device 1702. For example, a user may interact with the display 1712 or other controls of the surgical console 1704 to define material volumes to be delivered by and/or aspirated into the device 1702, flow rates associated with the device 1702, as well as other desired parameters associated with example arrangement 1700. In some instances, the surgical console 1704 may include other input devices, such as a keyboard and/or mouse, to allow the user to adjust control parameters for the arrangement 1700.

The surgical console 1704 may be configured to provide a user with a wide range of options regarding the control of outflow or inflow of materials from or to the device 1702, including, but not limited, to flow rate(s), single actuation volume, total volume, time for dispense (i.e., a preselected volume of material dispensed or aspirated in a preselected amount of time), etc. Single actuation volume, also referred to as dosage volume, is an amount of material dispensed (or aspirated) with a single actuation of an input device, such as foot pedal 1714. For example, a user may control the dosage volume in order to control an amount of material dispensed (or aspirated) with each actuation of the foot pedal 1714. This allows the user to make multiple, controlled injections or aspirations of a defined amount of material with the device 1702 during a procedure. A total volume of material contained within the device 1702 is understood to mean the total volume of material capable of being dispensed from or a total amount of material capable of being aspirated by the device 1702 during a procedure, regardless of the number of times the actuator has be actuated.

In some instances a user may select the desired control parameters prior to a procedure. Once the desired parameters are established, the user may control one or more aspects of the arrangement 1700, such as an operation of the device 1702, with the use of in input device, such as by actuating one or more mechanisms included on the foot pedal 1714. For example, the foot pedal 1714 may be used to cause a desired dosage and/or flow rate of material to be delivered by the system based on the selected parameters. This allows the arrangement 1700 to be customized to a user's desired preferences and/or for particular types of procedures. Further, as many eye procedures are performed with the user viewing the surgical site through a microscope, the user can, in some implementations, deliver or, in other implementations, aspirate a desired amount of material and/or a desired flow rate of material while focusing on the position of the device 1702 without having to look away from the microscope to adjust the device 1702.

The devices, systems, and methods described herein are suitable for injection or aspiration of numerous types of materials. Examples of such materials include, without limitation, anticoagulants, therapeutic drugs, anti-VEGF drugs, short-term retinal tamponades (e.g. perfluorocarbon liquid), long-term retinal tamponades (e.g. silicone oil, air/perfluorocarbon gas mixture) used in the repair of retinal detachments or tears, anti-infectives, anti-inflammatories, anti-infective/anti-inflammatories, and/or other materials. Other materials may also be used.

Although illustrative implementations have been shown and described, a wide range of modifications, changes, and substitutions are contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus comprising:
    a body defining a cavity for receiving a fluid, the body having a first opening providing communication between with the cavity and an exterior of the body;
    a structure movable within the cavity, the structure adapted to be displaced within the cavity to displace an amount of the material within the cavity;
    a lead screw comprising:
        a first portion coupled to the structure; and
        a longitudinal axis;
    a cam device coupled to the lead screw, the cam device comprising a plurality of cams;
    at least one engaging member adapted to engage the plurality of cams;
    an actuator coupled to the at least one engaging member, the actuator operable to oscillate the at least one engaging member to alternately engage the plurality of cams so as to rotate the cam device in a single direction; and
    an advancement component moveable between a first position in which the advancement component engages the lead screw and a second position in which the advancement component is disengaged from the lead screw, the advancement component comprising a first engaging feature, wherein the lead screw comprises a second engaging feature, and wherein the first engaging feature and the second engaging feature matingly engage to cause the lead screw to translate longitudinally along the longitudinal axis when the lead screw is rotated.

2. The apparatus of claim 1, wherein the plurality of cams comprises:
    a first plurality of cams disposed proximate a first end of the cam device; and
    a second plurality of cams disposed proximate a second end of the cam device;
    wherein the at least one engaging member engages one of the first plurality of cams when the at least one engaging member is moved towards the first end of the cam device to cause the cam device to rotate in a first angular direction; and
    wherein the at least one engaging member engages one of the plurality of the second plurality of cams when the at least one engaging member is moved towards the second end of the cam device to cause the cam device to rotate in the first angular direction.

3. The apparatus of claim 2, wherein each cam of the plurality of cams comprises an engagement surface operable contact the at least one engaging member, the engaging surface having a slope to cause a rotation to the cam device as the at least one engaging member slides along the engagement surface.

4. The apparatus of claim 2, wherein the first plurality of cams and the second plurality of cams are rotationally offset from each other about the longitudinal axis.

5. The apparatus of claim 1 further comprising an outer collar disposed circumjacent to the cam device and wherein the at least one engaging member radially extends from an interior surface of the outer collar.

6. The apparatus of claim 5, wherein the outer collar is coupled to the actuator and operable to move longitudinally relative to the cam device.

7. The apparatus of claim 1, wherein the first engaging feature is a threaded portion and wherein the second engaging feature is an outer threaded surface.

8. The apparatus of claim 1, wherein the advancement component comprises a slot and wherein the first engaging feature is formed on an interior surface of the slot.

9. The apparatus of claim 1, wherein the housing comprises a slot and wherein the advancement component is slideable within the slot between the first position in which the first engaging feature is engaged with the second engaging feature and the second position in which the first engaging feature is not engaged with the second engaging feature.

10. The apparatus of claim 1, wherein the cam device further comprises:
a central passage defining an interior wall; and
a protrusion extending inwardly from the interior wall, wherein the cam device comprises a longitudinally extending slot, wherein the cam device is coupled to the lead screw by receipt of the protrusion into the longitudinally extending slot.

11. The system of claim 1, wherein the lead screw is longitudinally slideable within a passage formed within the cam device and wherein the lead screw is rotationally fixed within the cam device.

12. The apparatus of claim 1 further comprising a needle defining a lumen, the needle coupled to the body such that the lumen is in communication with the first opening.

13. An apparatus comprising:
a body comprising:
a first cavity for receiving a fluid, the body having a first opening providing communication between with the first cavity and an exterior of the body;
a second cavity; and
a bore extending along a longitudinal axis, the bore providing communication between the first cavity and the second cavity;
a structure movable within the first cavity, the structure adapted to be displaced within the first cavity to displace an amount of the material within the first cavity;
a lead screw extending along the longitudinal axis through the bore, the lead screw comprising a first portion coupled to the structure;
a cam device disposed in the second cavity and rotatable therein, the cam device coupled to the lead screw, the cam device comprising a plurality of cams;
at least one engaging member adapted to engage the plurality of cams; and
an actuator coupled to the at least on engaging member, the actuator operable to oscillate the at least one engaging member to alternately engage the plurality of cams so as to rotate the cam device in a single direction,
wherein the actuator comprises a diaphragm that divides the second cavity into a first portion and a second portion, wherein an outer periphery of the diaphragm is coupled to an interior wall of the second cavity and an interior periphery of the diaphragm is coupled to an exterior surface of the outer collar.

14. The apparatus of claim 13 further comprising an advancement component, the advancement component comprising a first engaging feature, wherein the lead screw comprises a second engaging feature, and wherein the first engaging feature and the second engaging feature matingly engage to cause the lead screw to translate longitudinally along the longitudinal axis when the lead screw is rotated.

15. The apparatus of claim 14, wherein the first engaging feature is a threaded portion and wherein the second engaging feature is an outer threaded surface.

16. The apparatus of claim 14, wherein the advancement component comprises a slot and wherein the first engaging feature is formed on an interior surface of the slot.

17. The apparatus of claim 14, wherein the housing comprises a slot and wherein the advancement component is slideable within the slot between a first position in which the first engaging feature is engaged with the second engaging feature and a second position in which the first engaging feature is not engaged with the second engaging feature.

18. The apparatus of claim 13, wherein the plurality of cams comprises:
a first plurality of cams disposed proximate a first end of the cam device; and
a second plurality of cams disposed proximate a second end of the cam device;
wherein the at least one engaging member engages one of the first plurality of cams when the at least one engaging member is moved towards the first end of the cam device to cause the cam device to rotate in a first angular direction; and
wherein the at least one engaging member engages one of the plurality of the second plurality of cams when the at least one engaging member is moved towards the second end of the cam device to cause the cam device to rotate in the first angular direction.

19. The apparatus of claim 18, wherein each cam of the plurality of cams comprises an engagement surface operable contact the at least one engaging member, the engaging surface having a slope to cause a rotation to the cam device as the at least one engaging member slides along the engagement surface.

20. The apparatus of claim 18, wherein the first plurality of cams and the second plurality of cams are rotationally offset from each other about the longitudinal axis.

21. The apparatus of claim 13 further comprising an outer collar disposed in the second cavity and coupled to the actuator, the outer collar comprising a central bore defining an interior surface, wherein the cam device is disposed in the central bore, wherein the at least one engaging member extends radially inward from the interior surface.

22. The apparatus of claim 13, wherein the body further comprises a first passage that provides fluid communication with the first portion of the second cavity and a second passage that provides fluid communication with the second portion of the second cavity, wherein pneumatic pressure is alternately supplied to the first portion of the second cavity via the first passage and the second portion of the second cavity via the second passage to alternately displace the diaphragm in opposing directions thereby oscillating the outer collar.

23. The apparatus of claim 13, wherein the cam device further comprises:
a central passage defining an interior wall; and
a protrusion extending inwardly from the interior wall, wherein the cam device comprises a longitudinally extending slot, wherein the cam device is coupled to the lead screw by receipt of the protrusion into the longitudinally extending slot.

24. The apparatus of claim 13, wherein the lead screw is longitudinally slideable within a passage formed within the cam device and wherein the lead screw is rotationally fixed within the cam device.

25. The apparatus of claim 13 further comprising a needle defining a lumen, the needle coupled to the body such that the lumen is in communication with the first opening.

26. A method comprising:
oscillating at least one engagement member relative to a cam device, the cam device comprising a first plurality of cams and a second plurality of cams angularly offset from each other about a longitudinal axis;
engaging the at least one engaging member with the first plurality of cams in a first direction of the oscillation to rotate the cam device in a first direction;
engaging the at least one engaging member with the second plurality of cams in a second direction of the oscillation, the second direction opposite the first direction, to rotate the cam device in the first direction;
coupling a lead screw with the cam device such that the lead screw is longitudinally moveable relative to the cam device and rotationally fixed relative to the cam device; and
displacing the lead screw longitudinally relative to the cam device as the cam device is rotated in the first direction, causing a material to be displaced into or out of a cavity.

27. The method of claim 26 further comprising:
coupling a plunger to an end of the lead screw; and
displacing the plunger through the cavity in response to the longitudinal displacement of the lead screw, the cavity containing the material, and a portion of the material being displaced in the cavity by the plunger.

* * * * *